United States Patent [19]

Kinast et al.

[11] Patent Number: 4,808,622
[45] Date of Patent: * Feb. 28, 1989

[54] CIRCULATION ACTIVE METHIONINE-SUBSTITUTED 1,4-DIHYDROPYRIDINES

[75] Inventors: Günther Kinast; Eckhard Schwenner; Stanislav Kazda, all of Wuppertal; Andreas Knorr, Erkrath; Michael Kayser, Hagen, all of Fed. Rep. of Germany

[73] Assignee: Bayer Aktiengesellschaft, Leverkusen, Fed. Rep. of Germany

[*] Notice: The portion of the term of this patent subsequent to Dec. 27, 2005 has been disclaimed.

[21] Appl. No.: 1,496

[22] Filed: Jan. 7, 1987

[30] Foreign Application Priority Data

Jan. 11, 1986 [DE] Fed. Rep. of Germany ....... 3600594

[51] Int. Cl.[4] .................. C07D 211/86; A61K 31/455
[52] U.S. Cl. .................................... 514/356; 514/338; 546/271; 546/321; 546/14
[58] Field of Search .................. 546/321, 271, 14; 514/356, 338

[56] References Cited

U.S. PATENT DOCUMENTS 4,532,248  7/1985  Franckowiak et al. ............. 514/290

FOREIGN PATENT DOCUMENTS 0095451 11/1983 European Pat. Off. .
WO84/02132 6/1984 PCT Int'l Appl. .

*Primary Examiner*—Jane T. Fan
*Attorney, Agent, or Firm*—Sprung Horn Kramer & Woods

[57] ABSTRACT

Circulation active, e.g. antihypertensive novel methionine-substituted dihydropyridines of the formula

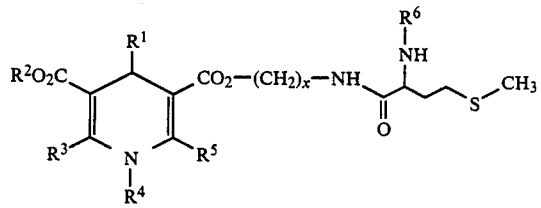

in which
  $R^1$ is phenyl or a heterocyclic radical, or a physiologically acceptable salt thereof.

17 Claims, No Drawings

CIRCULATION ACTIVE METHIONINE-SUBSTITUTED 1,4-DIHYDROPYRIDINES

The invention relates to methionine-substituted 1,4-dihydropyridines, to a process for the preparation and to their use in medicaments, in particular in medicaments affecting the circulation.

It is known that diethyl 1,4-dihydro-2,6-dimethyl-4-phenylpyridine-3,5-dicarboxylate is obtained when ethyl 2-benzylideneacetoacetate is reacted with ethyl β-aminocrotonate or ethyl acetoacetate with ammonia [E. Knoevenagel, Ber. dtsch. Chem. Ges. 31, 743 (1898)]. In addition, it is known that certain 1,4-dihydropyridines have interesting pharmacological properties (F. Bossert, W. Vater, Naturwissenschaften 58, 578 (1971)).

The present invention relates to methionine-substituted 1,4-dihydropyridines of the general formula (I)

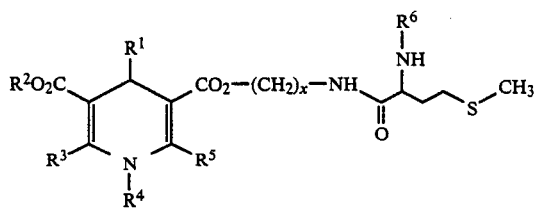

in which $R^1$ represents phenyl, naphthyl or represents thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, benzothiadiazolyl, quinolyl, isoquinolyl, quinazolyl or quinoxazolyl, it being possible for each of the said ring systems to be substituted by 1 or 2 identical or different substituents from the group comprising phenyl, straight-chain or branched alkyl having 1 to 8 carbon atoms, cycloalkyl having 3 to 7 carbon atoms, alkoxy having 1 to 4 carbon atoms, tri-, tetra- and pentamethylene, dioxymethylene, dioxyethylene, halogen, trifluoromethyl, trifluoromethoxy, difluoromethoxy, tetrafluoroethoxy, nitro, cyano, azido or $SO_m$-azido, in which m denotes a number from 0 to 2 and alkyl preferably contains 1 to 4 carbon atoms with, optionally, 1 to 3 fluorine atoms, $R^2$ represents a straight-chain, branched or cyclic, saturated or unsaturated, hydrocarbon radical which has up to 20 carbon atoms, is optionally interrupted in the chain by one oxygen atom or one sulphur atom and/or is optionally substituted by halogen, cyano, hydroxyl, acyloxy, nitro, nitrooxy or by a phenyl, phenoxy, phenylthio or phenylsulphonyl group each of which is optionally substituted by halogen, in particular fluorine, chlorine or bromine, cyano, dialkylamino each having 1 to 2 carbon atoms in each alkyl group, alkoxy having 1 to 4 carbon atoms, alkyl having 1 to 4 carbon atoms, trifluoromethyl or nitro, or $R^2$ is substituted by an α-, β- or γ-pyridyl group or by an amino group, this amino group carrying two identical or different substituents from the group comprising alkyl having up to 4 carbon atoms, alkoxyalkyl having up to 4 carbon atoms, phenyl and aralkyl, in particular benzyl, and these substituents optionally forming with the nitrogen atom a 5- to 7-membered ring which can contain as further heteroatom one oxygen or sulphur atom or N-phenyl or N-alkyl group, the alkyl group preferably comprising 1 to 3 carbon atoms, $R^3$ and $R^5$ are identical or different and each represents hydrogen, a straight-chain, branched or cyclic alkyl radical having up to 6 carbon atoms, a phenyl or benzyl radical, or one of the substituents $R^3$ or $R^5$ represents an alkyl radical which has up to 6 carbon atoms and is substituted by acetoxy or benzoyloxy, alkoxy or dialkoxy, each having up to 3 carbon atoms in each alkyl group, hydroxyl, amino, aminoalkoxy having up to 6 carbon atoms, phthalimido, phthalimidoalkoxy, piperidinoalkoxy, morpholinoalkoxy or N-phenyl-N'-piperazinoalkoxy, each having up to 6 carbon atoms in each alkoxy group, or represents the formyl or nitrile group, $R^4$ denotes hydrogen or a straight-chain or branched alkyl radical which has 1 to 4 carbon atoms, is optionally interrupted in the chain by one oxygen atom and/or is optionally substituted by a piperidino or morpholino radical, or represents a phenyl or benzyl radical, $R^6$ represents hydrogen or an amino protective group, and X represents a number from 2 to 16, and to their physiologically acceptable salts.

Preferred compounds of the general formula (I) are those in which $R^1$ represents phenyl, thienyl, furyl, pyridyl, quinolyl or benzoxadiazolyl, the said ring systems optionally being substituted by 1 to 2 identical or different substituents from the group comprising phenyl, alkyl having 1 to 2 carbon atoms, alkoxy having 1 to 2 carbon atoms, dioxymethylene, fluorine, chlorine, bromine or iodine, trifluoromethyl, trifluoromethoxy, difluoromethoxy, trifluoromethylsulphonyl, nitro, cyano, azido or alkylmercapto having 1 to 4 carbon atoms in the alkyl radical, $R^2$ represents a straight-chain, branched or cyclic, saturated or unsaturated, hydrocarbon radical which has up to 14 carbon atoms, is optionally interrupted in the chain by one oxygen atom and/or is optionally substituted by fluorine, chlorine, bromine, iodine, cyano, hydroxyl, acetoxy, nitrooxy or by a phenyl or phenoxy group which is optionally substituted by halogen, in particular fluorine or chlorine, alkoxy having 1 to 4 carbon atoms, alkyl having 1 to 4 carbon atoms or trifluoromethyl, or $R^2$ is substituted by an α-, β- or γ-pyridyl group or by an amino group, this amino group carrying two identical or different substituents from the group comprising alkyl having up to 4 carbon atoms, phenyl or aralkyl, in particular benzyl, $R^3$ and $R^5$ are identical or different and each represents hydrogen, a straight-chain, branched or cyclic alkyl radical having up to 6 carbon atoms, a phenyl or benzyl radical, or one of the substituents $R^3$ or $R^5$ represents an alkyl radical which has up to 4 carbon atoms and is substituted by acetoxy, methoxy, or dimethoxy, hydroxyl, amino, phthalimido, aminoalkoxy or phthalimidoalkoxy having, in each case, up to 4 carbon atoms in each alkoxy group, or represents the formyl or nitrile group, $R^4$ preferably denotes hydrogen or an alkyl radical which has up to 4 carbon atoms, is optionally interrupted in the chain by one oxygen atom and/or is optionally substituted by a morpholino radical, or represents a phenyl or benzyl radical, $R^6$ represents hydrogen or an amino protective group, and X represents a number from 2 to 12, and their physiologically acceptable salts.

Particularly preferred compounds of the general formula (I) are those in which $R^1$ represents phenyl, pyridyl or benzoxadiazolyl, the phenyl ring being substituted by 1 or 2 identical or different substituents from the group comprising chlorine, trifluoromethyl, nitro or cyano, $R^2$ represents a straight-chain, branched or cyclic hydrocarbon radical which has up to 7 carbon atoms, is optionally interrupted in the chain by one oxygen atom and/or is optionally substituted by fluorine, cyano, acetoxy, phenyl, phenoxy, α-, β- or γ-pyridyl or by an amino group, this amino group carrying two identical or different substituents from the group comprising alkyl having up to 4 carbon atoms and benzyl, $R^3$ and $R^5$ are identical or different and each represents a straight-chain or cyclic alkyl radical having up to 6 carbon atoms, or one of the substituents $R^3$ or $R^5$ represents an alkyl radical which has up to 2 carbon atoms and is substituted by acetoxy, hydroxyl, phthalimido, amino, phthalimidoethoxy or aminoethoxy, or represents the formyl or nitrile group, $R^4$ preferably represents hydrogen or the morpholinoethyl radical, $R^6$ represents hydrogen or an amino protective group, and X represents a number from 2 to 8,
and their physiologically acceptable salts.

Physiologically acceptable salts are salts of the compounds according to the invention with inorganic and organic acids. These preferably include inorganic mineral acids such as, for example, hydrochloric acid, hydrobromic acid, phosphoric acid and sulphuric acid, or organic carboxylic acids such as, for example, lactic acid, acetic acid, maleic acid, fumaric acid, citric acid, malic acid, succinic acid or benzoic acid.

When $R^6$ represents an amino protective group, then it is a protective group customary in peptide or β-lactam chemistry. These include vinyl, allyl, tert.-butyloxycarbonyl, benzyl, benzyloxycarbonyl, 2-nitro- or 4-nitro-benzyl, 2-nitro- or 4-nitro-benzyloxycarbonyl, 4-methoxyphenyl, formyl, benzoyl, acetyl, chloroacetyl, trichloroacetyl, trifluoroacetyl, methyloxycarbonyl, allyloxycarbonyl, trimethyl-, triethyl- or triphenylsilyl, tert.-butyl-dimethylsilyl, 2,4-dimethoxybenzyl, 2,4-dimethoxybenzyloxycarbonyl, 4-methoxybenzyl, 4-methoxymethyloxyphenyl, bis(4-methoxyphenyl)-methyl, tert.-butoxycarbonylmethyl, allyloxycarbonylmethyl, methoxymethyl, methylthiomethyl, methoxyethoxymethyl, [2-(trimethylsilyl)-ethoxy]methyl, 2-(methylthiomethoxy)ethoxycarbonyl or tetrahydropyranyl.

The compounds according to the invention exist in stereoisomeric forms which are either related as image and mirror image (enantiomers) or which are not related as image and mirror image (diastereomers). The invention relates to both the antipodes and the racemic forms as well as mixtures of diastereomers. The racemic forms can, just as can the diastereomers, be resolved in a known manner into the stereoisomerically homogeneous constituents (compare E. L. Eliel, Stereochemistry of Carbon Compounds, McGraw Hill, 1962).

The compounds according to the invention of the general formula (I) are prepared by reacting methionine compounds of the general formula (II)

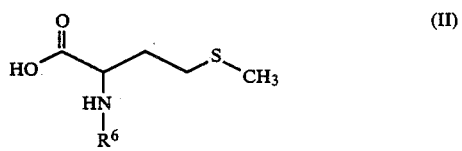

in which $R^6$ represents an amino protective group, after activation of the carboxyl group, for example by conversion into a mixed anhydride with pivaloyl chloride, ethyl or isobutyl chloroformate or by conversion into the mesylate by use of methanesulphonyl chloride or by conversion into an activated ester, for example with 1-hydroxybenzotriazole, N-hydroxysuccinimide or dicyclohexylcarbodiimide, reacts with dihydropyridines of the formula (III)

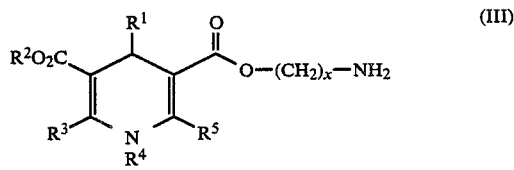

in which $R^1$–$R^5$ and X have the abovementioned meanings, in an inert solvent, where appropriate eliminates protective groups, and then where appropriate prepares the desired salts by reaction with acids.

The reaction can be illustrated by the following equation:

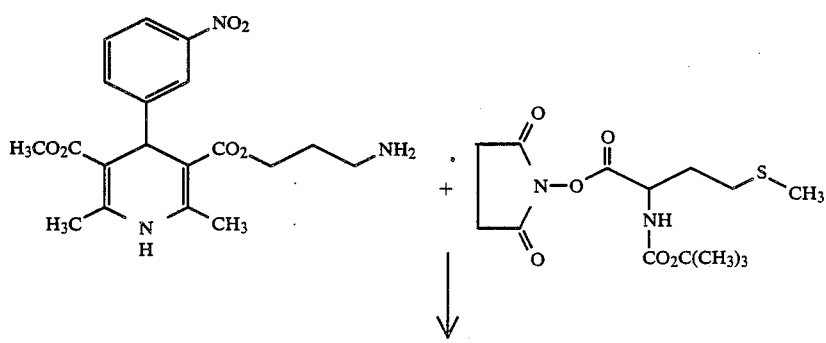

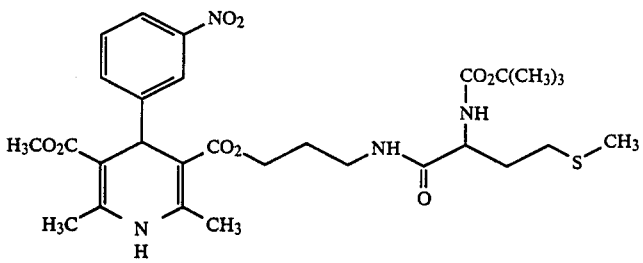

A large number of methods known from peptide chemistry can be used for coupling the methionine derivatives of the formula (II) to dihydropyridines of the formula (III) [Houben-Weyl's "Methoden der Organischen Chemie" ("Methods of Organic Chemistry"), XV/1 page 40].

It has proved to be advantageous for the methionine derivatives to be activated and then coupled with the dihydropyridines. Activation as the N-succinimidyl ester is particularly preferred.

Suitable solvents are the customary inert organic solvents which do not change under the reaction conditions. These preferably include alcohols such as methanol, ethanol, propanol or isopropanol, or ethers, such as diethyl ether, dioxane or tetrahydrofuran, or dimethylformamide, hexamethylphosphoric acid triamide, ethyl acetate, acetonitrile or acetone. However, it is also possible to use mixtures of the said solvents.

The reaction is carried out in a temperature range from $-30°$ C. to $+60°$ C., preferably from $-20°$ C. to $+20°$ C.

The reaction can be carried out under atmospheric or under elevated or reduced pressure. In general, it is carried out under atmospheric pressure.

It has proved favorable to carry out the reaction in a pH range of pH 7–pH 11. This is attained, where appropriate, by addition of a base such as triethylamine or by addition of buffer systems such as borate or phosphate buffer. However, it is perfectly possible to carry out the reaction without base or buffer.

In carrying out the process, in general 0.1 to 10, preferably 0.5–5, particularly preferably 1–1.5, mols of dihydropyridine, relative to 1 mol of methionine derivative, are used.

The dihydropyridines of the formula (III) which are used as starting materials are known or can be prepared by known methods [compare U.S. Pat. Specification No. 3,985,758, EP-AS (European Published Specification) 151,006].

The methionine derivatives of the formula (II) which are used as starting materials are known or can be prepared by known methods [Houben-Weyl's "Methoden der Organischen Chemie" ("Methods of Organic Chemistry") XV/1 page 46].

The methionine derivatives can be used for this purpose in their D-form, L-form or as DL mixture.

The compounds according to the invention have a broad and versatile spectrum of pharmacological actions.

Specifically, the following main actions have been detected in animal experiments:

1. The compounds bring about, on parenteral, oral or perlingual administration, a pronounced and long-lasting dilatation of the coronary vessels. This action on the coronary vessels is intensified by a simultaneous nitrite-like relieving effect on the heart. They affect or modify cardiac metabolism in the sense of saving energy.
2. The excitability of the pacemaking and conduction systems within the heart is reduced, resulting in an antifibrillatory action detectable at therapeutic doses.
3. The tone of the smooth muscles of the vessels is greatly diminished under the action of the compounds. The vasospasmolytic action can take place throughout the vascular system or manifest itself in more or less isolated vascular regions (such as, for example, the central nervous system). The compounds are thus particularly suitable as cerebral therapeutic agents.
4. The compounds lower the blood pressure in normotensive and hypertensive animals and can thus be used as antihypertensive agents.
5. Compounds have potent muscular spasmolytic actions which are evident on the smooth muscles of the stomach, intestinal tract, the urogenital tract and the respiratory system.
6. The compounds have a surprisingly high affinity for the 1,4-dihydropyridine receptors in the body, for example in the vessels, in the central nervous system, in the coronary region and in skeletal muscles. Their dissociation constants at body temperature for these receptors are more than one power of 10 lower than the dissociation constants of known dihydropyridines such as, for example, of nimodipine.

By reason of these properties, the compounds according to the invention are particularly suitable for the prophylaxis and therapy of acute and chronic ischaemic heart diseases in the widest sense, for the therapy of hypertension and for the treatment of disturbances of cerebral and peripheral blood flow.

The new active compounds can be converted in a known manner into the customary formulations, such as tablets, capsules, coated tablets, pills, granules, aerosols, syrups, emulsions, suspensions and solutions, using inert, non-toxic, pharmaceutically suitable vehicles or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid vehicles, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium laurylsulphate and talc can also be used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.001 to 1 mg/kg, preferably about 0.01 to 0.5 mg/kg, body weight to achieve effective results, and in the case of oral administration, the dosage is about 0.01 to 20 mg/kg, preferably 0.1 to 10 mg/kg, body weight.

Nevertheless, it can at times be necessary to deviate from the amounts mentioned, and in particular to do so as a function of the body weight of the experimental animal or of the nature of the administration method, but also because of the species of animal and its individual behavior towards the medicament, or the nature of the formulation of the medicament and the time or interval over which the administration takes place. Thus it can suffice in some cases to manage with less than the above-mentioned minimum amount, while in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

PREPARATION EXAMPLES

3-[2-(N-tert.-Butyloxy-carbonyl-L-methionyl)]-amino-ethyl 5-ethyl 1,4-dihydro-2,6-dimethyl-4-(2-trifluoromethylphenyl)-pyridine-3,5-dicarboxylate

Example 1

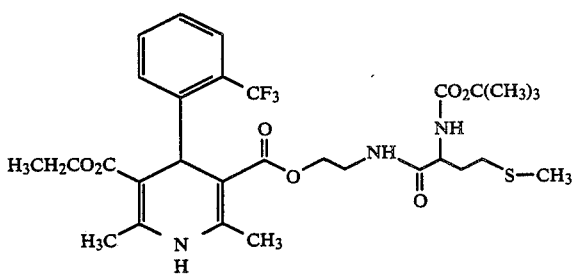

7.3 mmols of tert.-butoxycarbonyl-L-methionine N-succinimidyl ester and 7.3 mmols of 3-(2-aminoethyl) 5-ethyl 1,4-dihydro-2,6-dimethyl-4-(2-trifluoromethylphenyl)-pyridine-3,5-dicarboxylate are dissolved in 100 ml of methylene chloride, and the solution is stirred at room temperature for half an hour. Then 7.3 mmols of triethylamine are added, and the mixture is stirred at room temperature for a further hour. Then the organic phase is extracted by shaking successively with 100 ml of each of 10% strength citric acid solution, water, 10% strength sodium bicarbonate solution, water and with sodium chloride solution. The organic phase is dried over magnesium sulphate and evaporated.

Yield: 4.6 g.

Rf: 0.65 (CHCl₃/MeOH=10:1)

The examples which are listed below were prepared in analogy to Example 1. Examples 8 and 9 were synthesized starting from the enantiomerically pure dihydropyridine amine precursors in each case.

Example 2

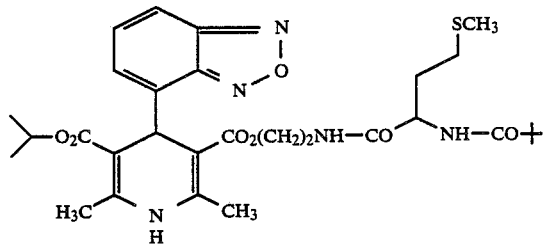

Yield: 87.7%

R$_f$: 0.408 (CHCl₃/MeOH 10:1)

| Analysis:   | C    | H   | N    | S   |
|-------------|------|-----|------|-----|
| calculated: | 57.0 | 6.5 | 11.1 | 5.1 |
| found:      | 56.9 | 6.6 | 11.0 | 4.8 |

Example 3
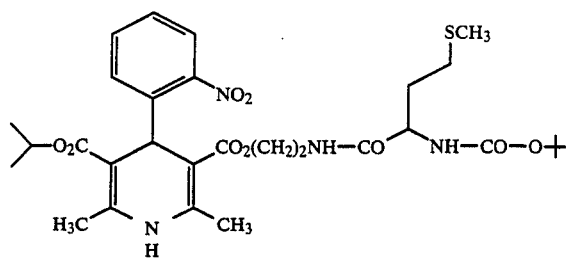
Yield: 89.16%
R_f: 0.362 (CHCl_3/MeOH 10:1)
| Analysis: | C | H | N | S |
|---|---|---|---|---|
| calculated: | 56.8 | 6.7 | 8.8 | 5.1 |
| found: | 56.6 | 6.7 | 8.8 | 5.0 |
Example 4
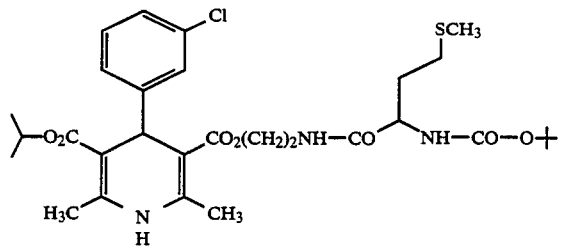
Yield: 89%
R_f: 0.42 (CHCl_3/MeOH 10:1)
| Analysis: | C | H | N | S |
|---|---|---|---|---|
| calculated: | 57.7 | 6.8 | 6.7 | 5.1 |
| found: | 57.8 | 6.8 | 6.7 | 5.1 |
Example 5
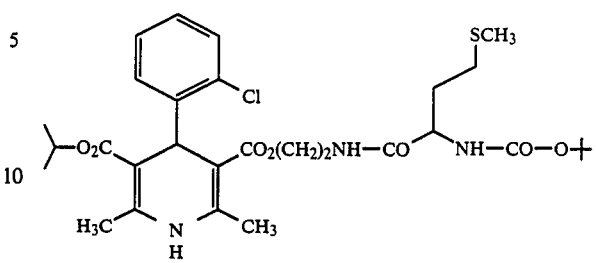
Yield: 88.89%
R_f: 0.484 (CHCl_3/MeOH 10:1)
| Analysis: | C | H | N | S |
|---|---|---|---|---|
| calculated: | 57.7 | 6.8 | 6.7 | 5.1 |
| found: | 57.3 | 6.8 | 6.7 | 5.1 |
Example 6
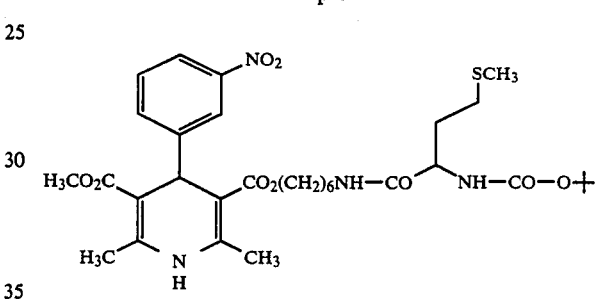
Yield: 87.6%
R_f: 0.475 (CHCl_3/MeOH 10:1)
| Analysis: | C | H | N | S |
|---|---|---|---|---|
| calculated: | 58.0 | 7.0 | 8.5 | 4.8 |
| found: | 57.6 | 7.0 | 8.4 | 4.9 |
Example 7
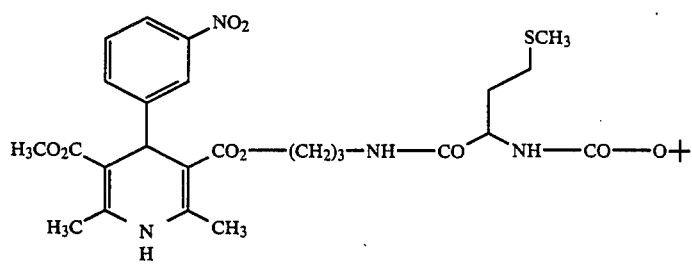
Yield: 80.16%
R_f: 0.429 (CHCl_3/MeOH 10:1)
| Analysis: | C | H | N | S |
|---|---|---|---|---|
| calculated: | 56.1 | 6.9 | 9.0 | 5.2 |
| found: | 55.9 | 6.6 | 8.9 | 5.1 |
Example 8

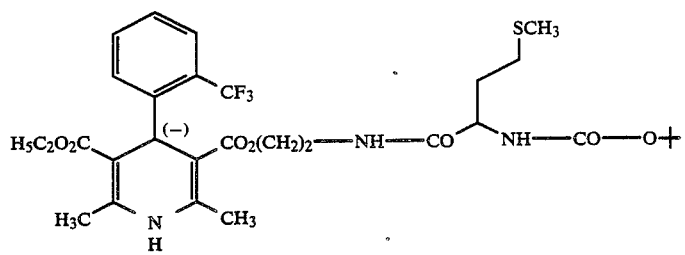

Yield: 96.5%
R_f: 0.65 (CHCl_3/MeOH 10:1)
$[\alpha]_D^{20}$: −86.06 in ethanol

| Analysis:   | C    | H   | F    | N   | S    |
|-------------|------|-----|------|-----|------|
| calculated: | 55.5 | 6.1 | 8.86 | 6.5 | 4.98 |
| found:      | 55.5 | 6.1 | 8.7  | 6.3 | 4.7  |

Example 9

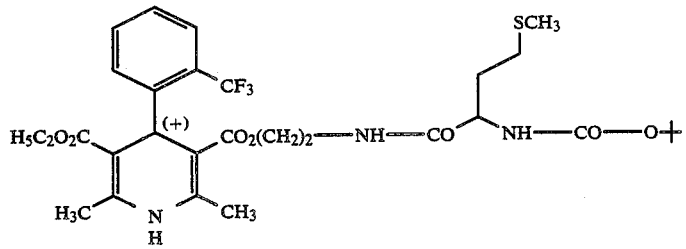

Yield: 95.3%
R_f: 0.64 (CHCl_3/MeOH 10:1)
$[\alpha]_D^{20}$: +53.7 in ethanol

| Analysis:   | C     | H    | F    | N   | S    |
|-------------|-------|------|------|-----|------|
| calculated: | 55.98 | 6.26 | 8.86 | 6.5 | 4.98 |
| found:      | 55.7  | 6.1  | 8.8  | 6.3 | 4.6  |

Example 10

3-[2-(L-Methionyl)-aminoethyl]5-ethyl 1,4-dihydro-2,6-dimethyl-4-(2-trifluoromethylphenyl)-pyridine-3,5-dicarboxylate

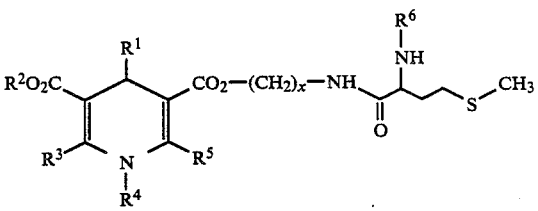

A mixture of 20 ml of trifluoroacetic acid and 15 ml of methylene chloride was added dropwise, within 10 minutes, to 7.2 g (11.2 mmols) of 3-[2-(N-tert.-butyloxycarbonyl-L-methionyl)aminoethyl]5-ethyl 1,4-dihydro-2,6-dimethyl-4-(2-trifluoromethylphenyl)-pyridine-3,5-dicarboxylate.

After stirring at room temperature for 2 hours, the mixture was extracted successively with 2N NaOH and water, and the organic phase was dried with sodium sulphate and evaporated.

Column chromatography on silica gel (40–60 μm) with chloroform/MeOH/ammonia=20/1/0.05 as eluting agent provided, after evaporation, the desired product as a foam.

Yield: 4.1 g (67.3%)

| Analysis:   | C    | H    | F    | N    | S   |
|-------------|------|------|------|------|-----|
| calculated: | 55.2 | 5.93 | 10.5 | 7.73 | 5.9 |
| found:      | 55.1 | 5.8  | 10.3 | 7.5  | 5.8 |

It will be understood that the specification and examples are illustrative but not limitative of the present invention and that other embodiments within the spirit and scope of the invention will suggest themselves to those skilled in the art.

We claim:

1. A methionine-substituted dihydropyridine of the formula $$\begin{array}{c}\text{structure}\end{array}$$

in which
R¹ represents benzooxadiazolyl, phenyl, naphthyl or phenyl or naphthyl substituted by 1 or 2 identical or different substituents from the group consisting of phenyl, straight-chain or branched alkyl having 1 to 8 carbon atoms, cycloalkyl having 3 to 7 carbon atoms, alkoxy having 1 to 4 carbon atoms, halogen, trifluoromethyl, trifluoromethoxy, difluoromethoxy, tetrafluoroethoxy, nitro, cyano, azido or SO_m-azido, in which m denotes a number from 0 to 2 and alkyl contains 1 to 4 carbon atoms with, optionally, 1 to 3 flourine atoms, $R^2$ represents a straight-chain, branched or cyclic, saturated or unsaturated, hydrocarbon radical which up to 20 carbon atoms, is optionally interrupted in the chain by one oxygen atom or one sulphur atom and/or is optionally substituted by halogen, cyano, hydroxyl, lower alkanoyloxy or nitro, or by a phenyl, phenoxy, phenylthio or phenylsulphonyl group each of which is optionally substituted by halogen, cyano, dialkylamino each having 1 to 2 carbon atoms in each alkyl group, alkoxy having 1 to 4 carbon atoms, alkyl having 1 to 4 carbon atoms, trifluoromethyl or nitro, or $R^2$ is substituted by an amino group, this amino group carrying two identical or different substituents from the group consisting of alkyl having up to 4 carbon atoms, alkoxyalkyl having up to 4 carbon atoms, phenyl and phenyl-lower alkyl, $R^3$ and $R^5$ are identical or different and each represents hydrogen, a straight-chain, branched or cyclic alkyl radical having up to 6 carbon atoms, a phenyl or benzyl radical, or one of the substituents $R^3$ or $R^5$ represents an alkyl radical which has up to 6 carbon atoms and is substituted by acetoxy or benzoyloxy, alkoxy or dialkoxy, each having up to 3 carbon atoms in each alkyl group, hydroxyl, amino or aminoalkoxy having up to 6 carbon atoms, or represents the formyl or nitrile group, $R^4$ denotes hydrogen or a straight-chain or branched alkyl radical which has 1 to 4 carbon atoms and is optionally interrupted in the chain by one oxygen atom, or represents a phenyl or benzyl radical, $R^6$ represents hydrogen or an amino protective group selected from the group consisting of vinyl, allyl, tert.-butyloxycarbonyl, benzyl, benzyloxycarbonyl, 2-nitro- or 4-nitro-benzyl, 2-nitro- or 4-nitrobenzyloxycarbonyl, 4-methoxyphenyl, formyl, benzoyl, acetyl, chloroacetyl, trichloroacetyl, trifluoroacetyl, methyloxycarbonyl, allyloxycarbonyl, trimethyl-, triethyl- or triphenylsilyl, tert.-butyl-dimethylsilyl, 2,4-dimethoxybenzyl, 2,4-dimethoxybenzyloxycarbonyl, 4-methoxybenzyl, 4-methoxymethyloxyphenyl, bis(4-methoxyphenyl)methyl, tert.-butoxycarbonylmethyl, allyloxycarbonylmethyl, methoxymethyl, methylthiomethyl, methoxyethoxymethyl, methyl, 2-(methylthiomethoxy)ethoxycarbonyl and tetrahydropyranyl, and X represents a number from 2 to 16, or a physiologically acceptable salt thereof.

2. A compound or salt according to claim 1, in which
$R^1$ represents phenyl or benzoxadiazolyl, or phenyl or benzoxadiazolyl substituted by 1 to 2 identical or different substituents from the group consisting of phenyl, alkyl having 1 to 2 carbon atoms, alkoxy having 1 to 2 carbon atoms, dioxymethylene, fluorine, chlorine, bromine or iodine, trifluoromethyl, trifluoromethoxy, difluoromethoxy, trifluoromethylsulphonyl, nitro, cyano, azido or alkylmercapto having 1 to 4 carbon atoms in the alkyl radical, $R^2$ represents a straight-chain, branched or cyclic, saturated or unsaturated, hydrocarbon radical which has up to 14 carbon atoms, is optionally interrupted in the chain by one oxygen atom and/or is optionally substituted by fluorine, chlorine, bromine, iodine, cyano, hydroxyl, acetoxy or by a phenyl or phenoxy group which is optionally substituted by halogen, in particular fluorine or chlorine, alkoxy having 1 to 4 carbon atoms, alkyl having 1 to 4 carbon atoms or trifluoromethyl, or $R^2$ is substituted by an amino group, this amino group carrying two identical or different substituents from the group consisting of alkyl having up to 4 carbon atoms, phenyl or benzyl, $R^3$ and $R^5$ are identical or different and each represents hydrogen, a straight-chain, branched or cyclic alkyl radical having up to 6 carbon atoms, a phenyl or benzyl radical, or one of the substituents $R^3$ or $R^5$ represents an alkyl radical which has up to 4 carbon atoms and is substituted by acetoxy, methoxy, or dimethoxy, hydroxyl, amino or aminoalkoxy having up to 4 carbon atoms in the alkoxy group, or represents the formyl or nitrile group, $R^4$ preferably denotes hydrogen or an alkyl radical which has up to 4 carbon atoms and is optionally interrupted in the chain by one oxygen atom, or represents a phenyl or benzyl radical, and X represents a number from 2 to 12.

3. A compound or salt according to claim 1, in which
$R^1$ represents phenyl or benzoxadiazolyl, the phenyl ring being substituted by 1 or 2 identical or different substituents from the group consisting of chlorine, trifluoromethyl, nitro or cyano, $R^2$ represents a straight-chain, branched or cyclic hydrocarbon radical which has up to 7 carbon atoms, is optionally interrupted in the chain by one oxygen atom and/or is optionally substituted by fluorine, cyano, acetoxy, phenyl, phenoxy or by an amino group, this amino group carrying two identical or different substituents from the group consisting of alkyl having up to 4 carbon atoms and benzyl, $R^3$ and $R^5$ are identical or different and each represents a straight-chain or cyclic alkyl radical having up to 6 carbon atoms, or one of the substituents $R^3$ or $R^5$ represents an alkyl radical which has up to 2 carbon atoms and is substituted by acetoxy, hydroxyl, amino, or aminoethoxy, or represents the formyl or nitrile group, $R^4$ represents hydrogen, and X represents a number from 2 to 8.

4. A compound according to claim 1 of the formula

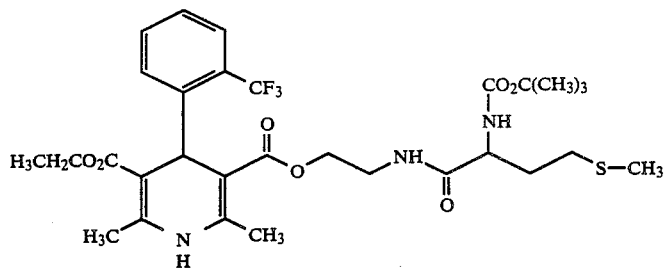

or a physiologically acceptable salt thereof.
5. A compound according to claim 1 of the formula

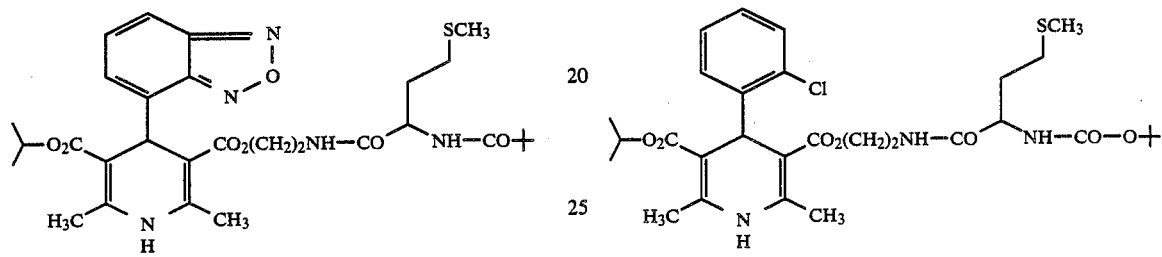

or a physiologically acceptable salt thereof.
6. A compound according to claim 1 of the formula

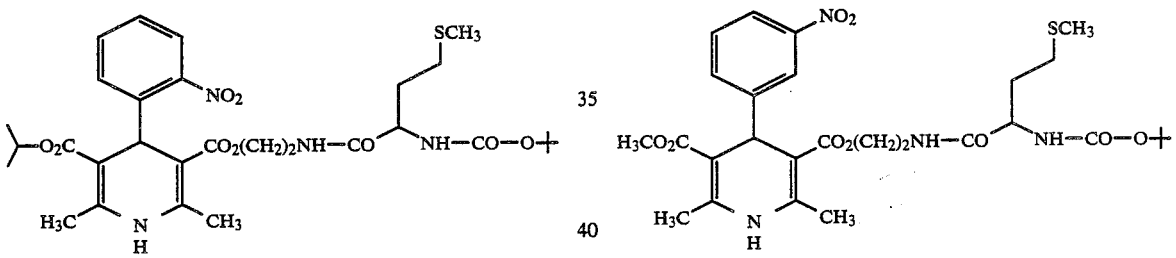

or a physiologically acceptable salt thereof.
7. A compound according to claim 1 of the formula

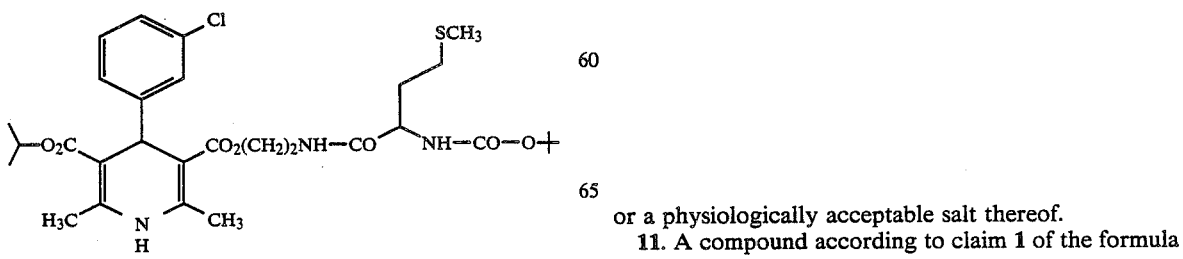

or a physiologically acceptable salt thereof.
8. A compound according to claim 1 of the formula or a physiologically acceptable salt thereof.
9. A compound according to claim 1 of the formula or a physiologically acceptable salt thereof.
10. A compound according to claim 1 of the formula

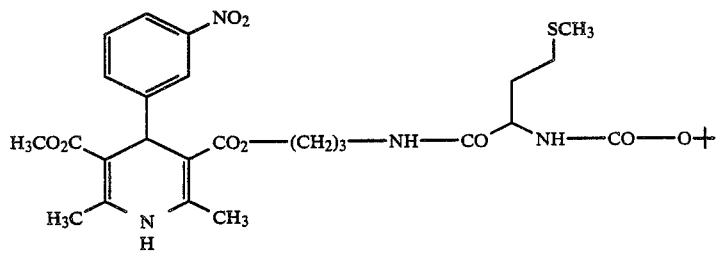

or a physiologically acceptable salt thereof.
11. A compound according to claim 1 of the formula

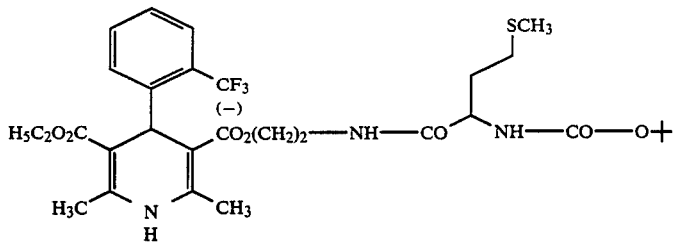

or a physiologically acceptable salt thereof.

12. A compound according to claim 1 of the formula

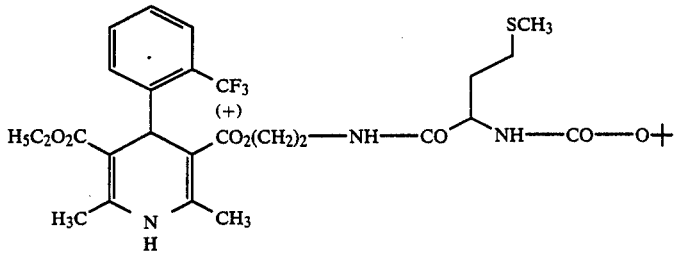

or a physiologically acceptable salt thereof.

13. A compound according to claim 1 of the formula

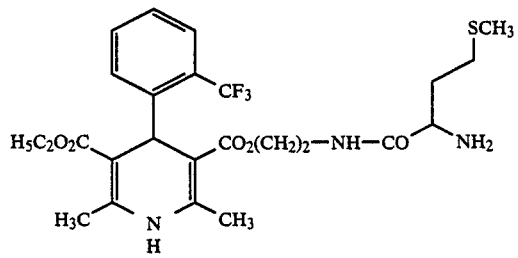

or a physiologically acceptable salt thereof.

14. A blood pressure-lowering composition comprising an effective amount therefor of a compound or salt according to claim 1 and a diluent.

15. A unit dose of a composition according to claim 14 in the form of a tablet, capsule or ampule.

16. A method of lowering the blood pressure in a patient in need thereof which comprises administering to such patient an effective amount therefor of a compound or salt according to claim 1.

17. The method according to claim 16, wherein such compound is

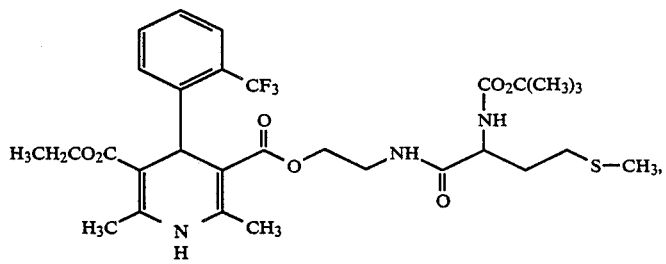

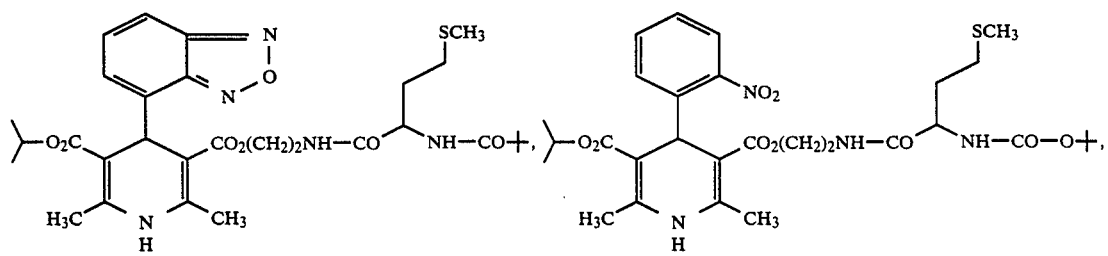

-continued
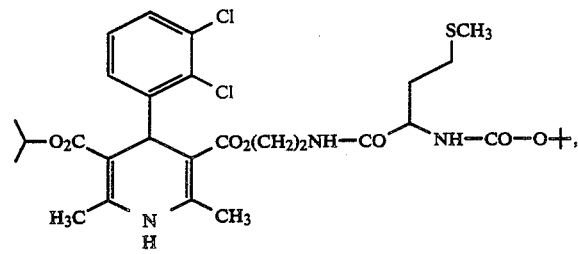
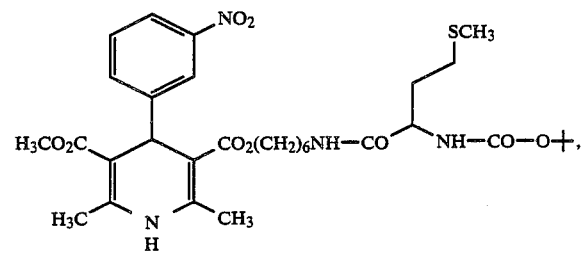
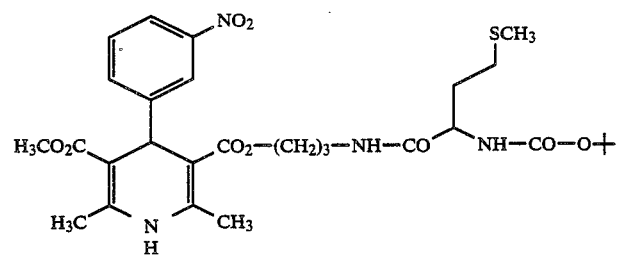
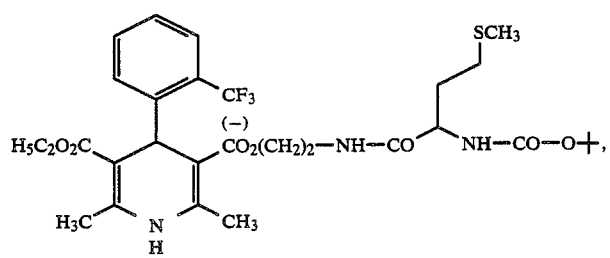
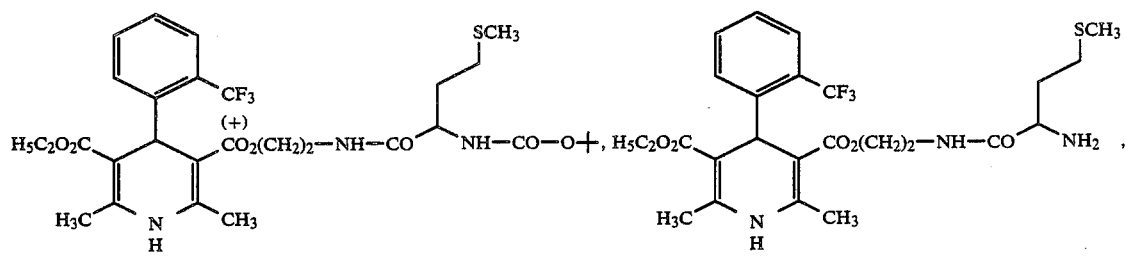
or a physiologically acceptable salt thereof.
* * * * *

UNITED STATES PATENT AND TRADEMARK OFFICE
CERTIFICATE OF CORRECTION

PATENT NO. : 4,808,622

DATED : February 28, 1989

INVENTOR(S) : Günther Kinast, et al

It is certified that error appears in the above-identified patent and that said Letters Patent is hereby corrected as shown below:

Col. 16, line 37      Middle of formula delete "$(CH_2)_2$" and substitute --$(CH_2)_6$--

Col. 19, line 1      Under "-continued" insert

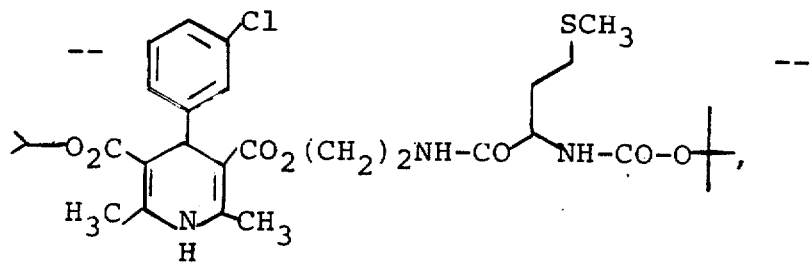

Col. 19, line 2      Delete top, left of formula and substitute

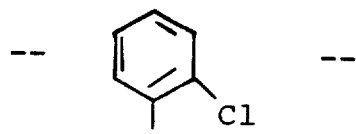

Signed and Sealed this

Twenty-third Day of January, 1990

Attest:

JEFFREY M. SAMUELS

Attesting Officer     Acting Commissioner of Patents and Trademarks